United States Patent [19]

Holtkamp, Sr.

[11] Patent Number: Plant 6,986

[45] Date of Patent: Aug. 15, 1989

[54] AFRICAN VIOLET PLANT NAMED LITTLE APATITE

[76] Inventor: Reinhold Holtkamp, Sr., Werther Strasse 112, D4294 Isselburg, Fed. Rep. of Germany

[21] Appl. No.: 251,250

[22] Filed: Sep. 30, 1988

[51] Int. Cl.[4] ..... A01H 5/00
[52] U.S. Cl. ..... Plt./69
[58] Field of Search ..... Plt./69

*Primary Examiner*—Robert E. Bagwill

*Attorney, Agent, or Firm*—Foley & Lardner, Schwartz, Jeffery, Schwaab, Mack, Blumenthal and Evans

[57] ABSTRACT

A new and distinct cultivar of African violet named Little Apatite characterized by its miniature growth habit; single, lilac flowers with darker touch in the center; violet-shaped flowers having elongated petals; strong stems which curve toward the center to form a compact bouquet above the leaves; profuse and continuous flowering; medium green spear to heart-shaped, slightly serrated leaves, flowering 10–11 weeks after planting of unrooted shoot, and by its long lasting and non-dropping flowers.

1 Drawing Sheet

The present invention comprises a new and distinct cultivar of African violet plant, botanically known as *Saintpaulia ionantha,* and hereinafter referred to by the cultivar name Little Apatite.

The new cultivar was referred to during the breeding and selection process by the designation I 402 and is a product of a planned breeding program. The new cultivar was originated from a cross made by me in the controlled breeding program in Haffen, Federal Republic of Germany. The female, or seed parent was a cultivar designated 4 Mini. The male, or pollen parent was a cultivar designated 69.

Little Apatite was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Little Apatite has not been observed under all possible environmental conditions. The phenotype may vary significantly with variations in environment such as temperature, light intensity and day length. The following observations, measurements and values describe the new cultivar as grown in a 4 cm pot in Haffen, West Germany and Nashville, Tenn. under greenhouse conditions which closely approximate those generally used in commercial practice.

The following traits have been repeatedly observed and are determined to be basic characteristics of Little Apatite, which in combination distinguish this African violet as a new and distinct cultivar:

(1) Little Apatite will not grow taller than 6 cm.
(2) Single lilac flowers with elongated petals.
(3) Strong wirelike and upright flower stems curving toward the center.
(4) First flash of flowers forms a tight bouquet above the leaves.
(5) Profuse flowering; under good growing conditions continuous flowering.
(6) Each plant carries 7–10 and more upright flower stems each of which carries 4 and more flowers.
(7) Long lasting, non-dropping flowers.

(8) Plant saleable 10 to 11 weeks after planting of unrooted shoot.
(9) Seed capsules push slightly through.
(10) Medium green hairy leaves.
(11) Spear to heart-shaped leaves are 2.0 to 2.5 cm in size.
(12) After maturity the flowers dry off, and remain on the peduncle.

The accompanying color photographic drawing shows a typical specimen plant of the new cultivar enlarged. The actual plant was grown in a 4 cm pot. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural sunlight conditions at approximately 2 p.m. in Nashville, Tenn.

Botanical classification: *Saintpaulia ionantha,* Ramat., c.v. Little Apatite.

Parentage:

*Male parent.*—69.

*Female parent.*—4 Mini.

Propagation: The new cultivar holds its distinguishing characteristics through successive propagations by leaf cuttings.

Plant: From 4 cm to 6 cm tall when grown in pots, and approximately 8–10 cm in diameter when fully grown.

*Leaves.*—General form: Spear to heart-shaped. Diameter: 20–22 mm wide and 23–25 mm long. Texture: Leatherlike. Aspect: Slightly serrated, shiny, hairy. Veins: Upperside: visible; underside: well pronounced light green, shiny. Color (upperside): Yellow-Green Group 146 A. Color (underside): Greyed-Green Group 193 A. Petiole: Strong, light green, occasionally purplish touch, hairy.

*Flowers.*—Buds: Size: 3–4 mm just before opening. Shape: Bell-shaped. Color: Lilac. Sepals; Five (5). Color: Purplish brown. Calyx: Shape: Funnel-shaped. Aspect: Spear-shaped, hairy. Peduncle: Character: Strong upright, hairy. Color:

Green with slight purplish touch. Individual flowers: Size: 22–24 mm. Shape: Single, violet-shaped, but with elongated petals; especially the 3 large ones are elongated. Color (upperside): Purple-Violet Group 82 between B and C. Under cooler temperatures and more intensive lighting, the lilac tends to intensify. Color (underside): Purple-Violet Group 82 D. Borne: Each flower stem carries 4 and more flowers on strong, upright peduncles that are free standing above the leaves, thereby forming a compact bouquet. Flowering habit: Flowers 10–11 weeks after planting an uprooted plantlet.

*Reproductive organs.*—Stamens: Two (2). Anthers: 2 composed of 4 anther cells, seed capsule pushes slightly through. Filaments: Yellowish green with purplish touch, 2 mm long. Styles: 4–5 mm long, purple, base of ovary light green and hairy.

*Roots.*—Normally developed, white when young, turning slightly brownish when older.

Disease resistance: Good.

General observations: Little Apatite is a super miniature violet, which does not grow taller than 6 cm. The single flowers are lilac with a darker touch in the center. They are violet-shaped, but have elongated petals, especially the 3 large petals. Occasionally 1–2 additional very small petals develop. The flowers are long-lasting and non-dropping. Under good growing conditions Little Apatite will bloom continuously. A nice bouquet of flowers free standing above the leaves develops approximately 10–11 weeks after planting an unrooted plantlet. Each of the 7–10 and more strong flower stems carries 4 and more flowers. The medium green leaves are spear to heart-shaped and slightly serrated.

I claim:

1. A new and distinct cultivar of African violet named Little Apatite, as described and illustrated, and particularly characterized by its miniature growth habit; single, lilac flowers with darker touch in the center; violet-shaped flowers having elongated petals; strong stems which curve toward the center to form a compact bouquet above the leaves; profuse and continuous flowering; medium green spear to heart-shaped, slightly serrated leaves; flowering 10–11 weeks after planting of unrooted shoot, and by its long lasting and non-dropping flowers.

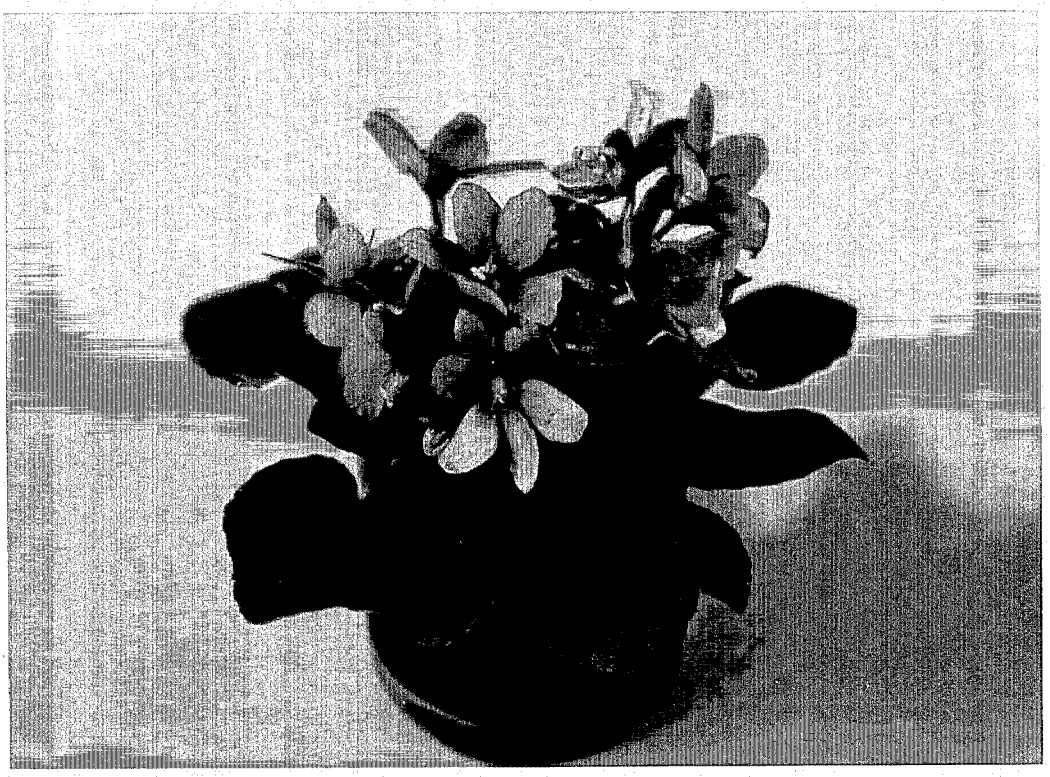

* * * * *